United States Patent
Lecocq et al.

(10) Patent No.: US 11,987,828 B2
(45) Date of Patent: *May 21, 2024

(54) METHOD FOR PRODUCING MALTITOL, WITH AN INCREASED YIELD

(71) Applicant: Roquette Freres, Lestrem (FR)

(72) Inventors: Aline Lecocq, La Madeleine (FR); Vincent Courbois, Bethune (FR)

(73) Assignee: ROQUETTE FRERES, Lestrem (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/742,353

(22) PCT Filed: Jul. 6, 2016

(86) PCT No.: PCT/FR2016/051704
§ 371 (c)(1),
(2) Date: Jan. 5, 2018

(87) PCT Pub. No.: WO2017/006049
PCT Pub. Date: Jan. 12, 2017

(65) Prior Publication Data
US 2018/0195098 A1    Jul. 12, 2018

(30) Foreign Application Priority Data
Jul. 6, 2015  (FR) ...................... 1556365

(51) Int. Cl.
| | |
|---|---|
| C12P 19/22 | (2006.01) |
| C07H 3/04 | (2006.01) |
| C12N 9/26 | (2006.01) |
| C12N 9/96 | (2006.01) |

(52) U.S. Cl.
CPC ............... *C12P 19/22* (2013.01); *C07H 3/04* (2013.01); *C12N 9/2425* (2013.01); *C12N 9/96* (2013.01); *C12Y 302/01002* (2013.01)

(58) Field of Classification Search
CPC ......... C12P 19/22; C12N 9/96; C12N 9/2425; C12Y 302/01002; C12Y 19/12
See application file for complete search history.

(56) References Cited

U.S. PATENT DOCUMENTS

| | | |
|---|---|---|
| 2,496,261 A | 2/1950 | Balls |
| 4,024,000 A | 5/1977 | Shibata et al. |
| 4,429,122 A | 1/1984 | Zupancic |
| 4,511,654 A | 4/1985 | Rohrbach et al. |
| 2005/0054071 A1* | 3/2005 | Udagawa ............. C12N 9/2408 435/200 |
| 2007/0237857 A1 | 10/2007 | Silver et al. |
| 2017/0121697 A1* | 5/2017 | Courbois ................ A23L 29/35 |

FOREIGN PATENT DOCUMENTS

| | | | |
|---|---|---|---|
| CN | 1225943 A | 8/1999 | |
| CN | 101544967 A | 9/2009 | |
| CN | 102399 763 A | 4/2012 | |
| CN | 102965358 A | 3/2013 | |
| EP | 0 735 042 A1 | 10/1996 | |
| EP | 0 905 138 A1 | 3/1999 | |
| EP | 2 055 197 A1 | 5/2009 | |
| EP | 2 093 231 A1 | 8/2009 | |
| FR | 2 905 705 A1 | 3/2008 | |
| FR | 2 994 440 A1 | 2/2014 | |
| JP | 55-039708 | * 3/1980 | ............. C12P 19/14 |
| WO | WO 95/10627 A1 | 4/1995 | |
| WO | WO 2009/112740 A2 | 9/2009 | |
| WO | 2013/114219 A2 | 8/2013 | |
| WO | WO 2013/114219 A2 | 8/2013 | |
| WO | WO 2013/114223 A2 | 8/2013 | |
| WO | WO 2013/148152 A1 | 10/2013 | |

OTHER PUBLICATIONS

Danisco Product Description-PD 215918-5.6EN Diazyme Fa, pp. 1-3, downloaded from http://www.mags.datagraf.dk/epub/files/brewing%20e-guide/diazyme_fa.pdf on Jun. 26, 2019 (Year: 2010).*
Olempska-Beer, Z. Isoamylase From Psudomonas Amyloderamosa Chemical and Technical Assessment; 68th JECFA, pp. 1-6, downloaded from: https://www.fao.org/fileadmin/templates/agns/pdf/jecfa/cta/68/Isoamylase.pdf on Feb. 16, 2023. (Year: 2007).*
Brown et al. Kinetic Study of the Thermal Denaturation of a Hyperthermostable Extracellular Alpha-Amylase From Pyrococcus Furiosus; Biochimical et Biophysica Acta, vol. 1834, pp. 2600-2605. (Year: 2013).*
J. S. Tolan et al., "Cellulase from Submerged Fermentation." Advances in Biochemical Engineering/Biotechnology, vol. 65, pp. 41-67, 1999.
Oct. 19, 2020 Office Action issue in Chinese Application No. 2020101402007590.
D. E. Bilderback, "A Simple Method to Differentiate between a- and b-Amylase," Plant Physiol., vol. 51, pp. 594-595, 1973.
Nov. 29, 2023 Office Action issued in U.S. Appl. No. 17/852,965.

* cited by examiner

*Primary Examiner* — Jeanette M Lieb
*Assistant Examiner* — Paul C Martin
(74) *Attorney, Agent, or Firm* — Oliff PLC

(57) ABSTRACT

A process for producing maltitol includes at least: producing a maltose syrup, by hydrolysis of a granular starch, in a first stage of liquefaction of granular starch to form a liquefied starch, followed by a stage of saccharification of the liquefied starch to which an aqueous solution of beta-amylase has been added, to form the maltose syrup; hydrogenating the maltose syrup to form an aqueous maltitol composition; and recovering the maltitol composition. The aqueous solution of beta-amylase also includes potassium sorbate, glycerol, and sodium carbonate.

15 Claims, No Drawings

METHOD FOR PRODUCING MALTITOL, WITH AN INCREASED YIELD

CROSS REFERENCE TO RELATED APPLICATIONS

This application is a U.S. national stage application of International patent application No. PCT/FR2016/051704, filed Jul. 6, 2016, which claims the priority of French application No. 1556365, filed on Jul. 6, 2015, the subject matters of which are incorporated in their entirety by reference herein.

FIELD OF THE INVENTION

The present invention relates to a process for producing maltitol, obtained from a maltose syrup produced by enzymatic hydrolysis of a starch by means of a particular stabilized beta-amylase aqueous solution. This process has an improved maltitol yield.

PRIOR ART

Maltitol is a polyol which is highly beneficial, due to the fact that it is less calorific than sucrose while advantageously having organoleptic properties very close to those of this sugar; moreover, it is also more chemically stable than sucrose. In addition, maltitol has the particular feature of being non-cariogenic, which enables it to be used in multiple industrial applications, especially in the food and pharmaceutical industries.

Maltitol is obtained industrially by a step of hydrogenation of maltose. Generally, a maltitol syrup is obtained from a maltose syrup, the richness in the maltose syrup subjected to the hydrogenation step determining the maltitol richness of the hydrogenated syrup obtained. The maltitol syrup may be used as is; however, it is generally enriched in maltitol using fractionation techniques, especially by continuous chromatography, or else by crystallizing the hydrogenated syrup, the latter having been optionally enriched in maltitol beforehand.

As regards the first step of producing a maltose syrup, it may comprise at least one step of hydrolysis of a granular starch, said process generally comprising a step of enzymatic hydrolysis using a maltogenic enzyme. This enzyme may be a beta-amylase.

Beta-amylases are exohydrolases which release maltose units from the nonreducing beta-ends of $\alpha$-1$\rightarrow$4-linked glucose polymers or oligomers, the reaction stopping at the first point of $\alpha$-1$\rightarrow$6 branching encountered. Major components of the "diastatic power" (corresponding to the combined activities of alpha-amylases, beta-amylases, alpha-glucosidases and debranching enzymes) during malting (artificial germination of cereal seeds), the beta-amylase activities isolated from this enzymatic cocktail are essential for the production of maltose generated from starch.

The saccharifying activity of beta-amylases alone is therefore made use of industrially for the production of maltose.

Thus, it is understood from the above text that obtaining a syrup with a high maltose content is particularly advantageous when it is desired to produce maltitol. Indeed, if it is desired to increase the maltitol yield of a process, one possibility is to increase the maltose richness in the syrup produced by enzymatic hydrolysis of the starch.

Thus, processes for producing maltitol which seek to obtain syrups having a high maltose richness have been described in numerous documents.

By way of example, mention may be made of application WO 2013/148152 which describes a process for producing a maltose-rich syrup from granular starch comprising a first step of dissolving granular starch using an exogenous alpha-amylase to form a mixture of dextrins, and a second step of hydrolysis of this mixture of dextrins by means of a maltogenic enzyme, which may be a beta-amylase, according to a particular alpha-amylase/maltogenic enzyme ratio.

There are numerous processes for producing beta-amylases. It is thus known that ungerminated barley, rye or wheat seeds are all biological materials of choice for the large-scale commercial preparation of beta-amylases. It is, moreover, known to those skilled in the art that half of the beta-amylases that can be extracted from the ungerminated seeds can be readily obtained in the form of free enzymes by extraction with water and saline solutions. The other half is partly in "bound" form which requires the addition of reducing agents or proteolytic enzymes for the extraction thereof. Another beta-amylase fraction that is not directly extractable, referred to as the "latent" fraction, has also been described: detergents are necessary in order to extract it from cereal seeds. Moreover, the beta-amylase extraction processes described in the prior art are adapted according to the intended application.

In industrial processes, after the extraction thereof, the beta-amylase is systematically stored before being used. This storage may last at least one day, or even at least one week, or else at least one month.

However, it then turns out that the enzymatic activity of the beta-amylase will decrease over time. It is recalled that the activity of an enzyme is, by definition, the amount of substrate transformed (or of product formed) per unit time and under the optimum operating conditions for the enzyme (temperature, pH, etc.). This value therefore quantifies the effectiveness of the enzyme. Conventionally, the enzymatic activity is measured via determining another parameter: diastatic activity. The latter is expressed in degrees of diastatic power (° DP), defined as the amount of enzyme contained in 0.1 ml of a 5 wt % solution of a sample of enzyme preparation sufficient to reduce 5 ml of Fehling's solution, when said sample is placed in 100 ml of the substrate for 1 h at 20° C.

A number of documents are currently known, describing processes for obtaining beta-amylase with a view to improving the stability thereof in terms of the enzymatic activity thereof.

Document CN102965358 discloses a process for obtaining, from soybean, a beta-amylase by precipitation, then draining, clarification and ultrafiltration. Said process uses calcium chloride, and optionally sulfuric acid salts, in the precipitation step.

Document CN102399763 describes the production of beta-amylase from bran, with addition of calcium chloride and sodium hydrogen phosphate, then concentration and stabilization in the presence of sorbitol and of potassium sorbate, before sterilization.

Document CN101544967 discloses a process for producing beta-amylases by precipitation, separation and centrifugation, and subsequently recommends the addition of calcium chloride, of orthophosphoric acid, of diatomaceous earth and of glycerol.

Document CN1225943 describes a process for preparing beta-amylase comprising the steps of ultrafiltration, concentration and precipitation of soybean powder extracts, the precipitation being preceded by the addition of sodium sulfate and the regulation of the pH to between 3.6 and 5.

Document U.S. Pat. No. 2,496,261 describes a process for obtaining beta-amylase from sweet potato, which comprises a step of precipitation in the presence of ammonium sulfate then acidification with hydrochloric acid.

Document U.S. Pat. No. 4,024,000 describes a process for preparing beta-amylase which employs divalent or trivalent ions selected from calcium, magnesium, barium or aluminum hydroxides and the salts thereof, and regulation of the pH to a range of between 4.5 and 8.

However, it should be noted that none of these solutions makes it possible to obtain a beta-amylase preparation in the form of an aqueous solution which is sufficiently stable over time to satisfactorily maintain the enzymatic activity thereof.

While continuing its research, the applicant has been able to demonstrate that a most particular selection of additives makes it possible to achieve such an objective. The aqueous solution of beta-amylase stabilized with these additives therefore has, for an equivalent storage duration, a better enzymatic activity than the aqueous solutions of beta-amylase which are already known.

Thus, as beta-amylase is systematically stored before use in industrial processes, the applicant has achieved a process for producing maltitol which makes it possible to improve the yield, one step of which comprises enzymatic hydrolysis of starch using the stablilized aqueous solution of beta-amylase.

SUMMARY OF THE INVENTION

Thus, the subject of the invention is a process for producing maltitol, comprising: a) a step of producing a maltose syrup, referred to as "maltose syrup A", by hydrolysis of a granular starch, this step comprising a first stage of liquefaction of said granular starch by hydrolysis to form a liquefied starch, followed by a stage of saccharification of the liquefied starch to form the maltose syrup A;
- b) optionally subjecting the maltose syrup A to a step of concentration, of dilution, of enrichment in maltose, and/or of mixing with another starch hydrolyzate syrup to form another maltose syrup, referred to as "maltose syrup B";
- c) a step of hydrogenation of the maltose syrup A or of the maltose syrup B to form an aqueous composition of maltitol, referred to as "maltitol composition C";
- d) optionally subjecting the maltitol composition C to a step of concentration, of dilution, of enrichment in maltitol, and/or of mixing with an additional polyol syrup to form an aqueous maltitol composition, referred to as "maltitol composition D";
- e) optionally a step of formation of maltitol powder from the maltitol composition C or from the maltitol composition D;
- f) a step of recovering the maltitol composition C, the maltitol composition D or the maltitol powder; wherein the stage of saccharification of the liquefied starch comprises the introduction, into the liquefied starch, of an aqueous solution of beta-amylase, also comprising:
potassium sorbate;
glycerol;
sodium carbonate.

Indeed, this process may make it possible to obtain, compared to similar processes using already known solutions of beta-amylase, compositions having a greater maltitol richness. The process according to the invention also makes it possible to reduce, or even eliminate, steps of enrichment in maltitol and/or in maltose. It may also make it possible to reduce the duration of the step a). The process according to the invention makes it possible to obtain at least one of these advantages, said advantages contributing to improving the maltitol yield of this process.

DETAILED DESCRIPTION OF THE INVENTION

As described above, the process according to the invention relates to a process for producing maltitol, one step of which involves the enzymatic hydrolysis of a starch by means of a particular aqueous solution of beta-amylase.

The first step of the process according to the invention comprises a step a) of producing a maltose syrup by hydrolysis of a granular starch.

According to the present invention, the term "starch" comprises all types of starch, which of course includes flours. The granular starch may be of any botanical origin, and especially may originate from corn, potato, sweet potato, wheat, rice, pea, broad bean, horse bean, cassava, sorghum, konjac, rye, buckwheat and barley, advantageously from wheat, corn, pea or potato.

This step of hydrolysis of a granular starch comprises a first stage of liquefaction of said granular starch by hydrolysis to form a liquefied starch, followed by a stage of saccharification of the liquefied starch to form the maltose syrup.

During the liquefaction stage, this granular starch is generally put in the form of a starch milk, that is to say a suspension of granular starch in water. This starch milk generally has acid added to it in the case of what is referred to as acid liquefaction, or has an enzyme added to it, in the case of an enzymatic liquefaction.

The starch liquefaction stage is preferably carried out by enzymatic hydrolysis by means of an alpha-amylase.

In the process in accordance with the invention, it is preferred to carry out a controlled hydrolysis of the starch milk, so as to obtain a liquefied starch with a low degree of transformation. Thus, the conditions of temperature, of pH, of enzyme and calcium content, which are known to those skilled in the art, are determined such that they make it possible to obtain a liquefied starch with a low DE (Dextrose Equivalent), generally less than 10, preferably less than 7, for example less than 4.

By way of example, the liquefaction stage may be carried out in at least two sub-steps, the first consisting in heating, for a few minutes and at a temperature of between 105 and 108° C., the starch milk in the presence of an alpha-amylase (of the TERMAMYL 120 L type, sold by Novozymes) and of a calcium-based activator, the second sub-step consisting in heating the starch milk treated in this way to a temperature of between 95 and 100° C. for one to two hours. Once the liquefaction step has finished and the liquefied starch has been obtained, under the conditions of dry matter content, of pH, of enzyme and calcium content which are well known to those skilled in the art, the alpha-amylase may be inhibited. This inhibition of the alpha-amylase may preferably be carried out thermally, by performing, at the end of the liquefaction, a heat shock for a few seconds at a temperature of greater than or equal to 130° C.

After the first stage of liquefaction of said granular starch, the liquefied starch obtained is subjected to a saccharification stage to form the maltose syrup.

According to the invention, the stage of saccharification of the liquefied starch comprises the introduction, into the liquefied starch, of an aqueous solution of beta-amylase, also comprising:

potassium sorbate;

glycerol;

sodium carbonate.

The aqueous solution of beta-amylase of use in this step may advantageously comprise:

a) from 0.05 to 0.5%, preferentially from 0.1 to 0.3%, and very preferentially approximately 0.2%, of potassium sorbate;

b) from 30 to 50%, preferentially from 35 to 45%, and very preferentially approximately 40%, of glycerol;

c) from 0.05 to 0.5%, preferentially from 0.1 to 0.3%, and very preferentially approximately 0.2%, of sodium carbonate;

these percentages being expressed as dry weight of each constituent relative to the total weight of said aqueous solution of beta-amylase.

The aqueous solution of beta-amylase of use in the invention advantageously comprises, relative to the total weight thereof, a dry weight of beta-amylase within the range extending from 5 to 20%, preferentially from 10 to 20%, very preferentially approximately 15% of the total weight thereof.

Although the aqueous solution of beta-amylase of use in the invention may optionally comprise constituents other than water and the constituents described above, according to one embodiment it consists of a mixture:

of 0.05 to 0.5% by weight, preferentially from 0.1 to 0.3%, and very preferentially approximately 0.2%, of potassium sorbate;

of 30 to 50% by weight, preferentially from 35 to 45%, and very preferentially approximately 40%, of glycerol;

of 0.05 to 0.5% by weight, preferentially from 0.1 to 0.3%, and very preferentially approximately 0.2%, of sodium carbonate;

of 5 to 20% by weight, preferentially from 10 to 20%, very preferentially approximately 15%, of beta-amylase;

of 35 to 50% by weight, preferentially from 40 to 45%, of water.

The aqueous solution of beta-amylase has excellent stability, which enables it to maintain its enzymatic activity over time. Thus, the process according to the invention may comprise a step of storage, which may be carried out at room temperature or under temperature-controlled conditions, for a time of at least one day before introduction into the liquefied starch, advantageously for a time ranging from 1 to 300 days, optionally from 10 to 250 days, especially from 30 to 200 days, for example from 60 to 150 days.

This time is defined as the time between the end of producing the stabilized beta-amylase and the moment at which it is introduced into the liquefied starch during the process.

The aqueous solution of beta-amylase of use in the invention may be produced by simply mixing the additives (potassium sorbate, glycerol and sodium carbonate) with the beta-amylase, for example by introducing and mixing them into a non-stabilized aqueous beta-amylase solution, the mixing being able to be carried out very simply at room temperature. The potassium sorbate, the glycerol and the sodium carbonate are preferentially in the form of aqueous solutions. Those skilled in the art will know how to adapt the solids extract of these solutions relative to the solubility of the products but also so as to limit the viscosity of these solutions and so as to make it readily handleable and especially pumpable.

For example, the beta-amylase may be obtained in the form of a non-stabilized beta-amylase aqueous solution by the steps consisting in:

providing a soluble fraction of starch plants;

carrying out, on said soluble fraction, a step of microfiltration in order to obtain a microfiltration permeate;

carrying out, on the microfiltration permeate, a step of ultrafiltration in order to obtain an ultrafiltration retentate.

It is thus said ultrafiltration retentate which generally constitutes said non-stabilized beta-amylase aqueous solution, into which the potassium sorbate, the glycerol and the sodium carbonate may be introduced.

Moreover, it is desirable to keep said solution of beta-amylase as obtained at a temperature of less than 15° C., preferentially less than 10° C., ideally at around 5° C., so as to further improve the maintenance of the enzymatic activity thereof.

It is also desirable to prepare the aqueous solution of use in the invention as quickly as possible after obtaining the non-stabilized beta-amylase solution, so as to further improve the enzymatic activity thereof, preferably within a time of less than 1 day.

According to the invention, the stage of saccharification of the liquefied starch may be carried out conventionally, aside from the fact that it is carried out by means of the stabilized solution of beta-amylase described above.

The stage of saccharification may be carried out in the presence of at least one additional enzyme, this enzyme being for example selected from maltogenic alpha-amylases, fungal alpha-amylases and/or debranching enzymes.

The enzymes may be added in one single go or in several goes, simultaneously.

By way of example of maltogenic alpha-amylase, mention may be made of that sold by Novozymes under the name Maltogenase 5.

The debranching enzyme may be selected from the group consisting of pullulanases and isoamylases. The pullulanase is, for example, that sold by ABM under the name PULLUZYMER. The isoamylase is, for example, that sold by HAYASHIBARA.

The additional enzyme(s) may be introduced simultaneously into the liquefied starch milk, before or after the stabilized solution of beta-amylase.

For example, maltogenic alpha-amylase may first be added, then the stabilized solution of beta-amylase may be added. In this case, if a debranching enzyme is added, the adding may be carried out at the moment at which the maltogenic alpha-amylase is added, at the moment at which the beta-amylase is added, or else subsequently.

During the saccharification stage, it is possible to monitor the content of the different hexoses, and to cause the proportion of the contents to change by selecting the additional enzymes and by adjusting the amounts of enzymes.

According to a first embodiment, the stabilized beta-amylase solution is introduced at the same time as the additional enzyme(s).

According to a second embodiment, the liquefied starch milk is first subjected to the action of a maltogenic alpha-amylase. During this first saccharification step, the maltogenic alpha-amylase may be added in a single go or in several goes. Then, after having left the maltogenic alpha-amylase to act, the saccharification of the liquefied starch milk is carried out by means of the stabilized beta-amylase solution described above.

Alternatively, according to a third embodiment, it is possible to subject the liquefied starch milk to the action of the stabilized beta-amylase solution described above. During this first saccharification step, the stabilized beta-amylase solution may be added in a single go or in several goes. Then, after having left the stabilized beta-amylase solution to act, the saccharification of the liquefied starch milk is carried out by means of a maltogenic alpha-amylase.

It is also possible to combine an enzyme which specifically hydrolyzes the alpha-1,6-bonds of the starch, also referred to as a "debranching enzyme", with the enzymes having a maltogenic activity (maltogenic alpha-amylase and beta-amylase). This addition of a debranching enzyme makes it possible, on the one hand, to accelerate the hydrolysis reactions without simultaneously accelerating the reversion reactions and, on the other hand, to reduce the amount of highly-branched oligosaccharides which usually resist the action of maltogenic enzymes. This debranching enzyme may especially be a pullulanase or an isoamylase. Advantageously, the saccharification stage is carried out in the presence of isoamylase, for which the applicant company has observed that it makes it possible not only to obtain a maltose syrup having a higher maltose content than when using a pullulanase, but also to obtain a maltose syrup having a reduced content of maltosyl-1,6-maltose (and hence in maltosyl-1,6-maltitol after hydrogenation).

The hydrolyzate saccharified in this way is then generally filtered, for example by using a precoat filter or membrane microfiltration. The hydrolyzate may also be demineralized. According to the invention, at the end of step a), a maltose syrup A is obtained.

The process optionally comprises a step b) in which the maltose syrup A is subjected to a step of concentration, of dilution, of enrichment in maltose, and/or of mixing with an additional starch hydrolyzate syrup to form an aqueous maltose composition B. A step of concentration of the syrup consists in increasing the dry matter thereof by partial evaporation of the water present in the syrup, while a step of dilution consists in reducing the dry matter content by adding water. It is optionally possible to enrich the syrup in maltose, especially by using molecular sieving. This step of molecular sieving may thus make it possible to recover:
  either a first fraction enriched in maltose and higher oligosaccharides and a second fraction enriched in glucose;
  or a first fraction enriched in higher oligosaccharides and a second fraction enriched in maltose and glucose;
  or, finally, a first fraction enriched in higher oligosaccharides, a second fraction enriched in maltose and a third fraction enriched in glucose.

This step of molecular sieving may consist, for example, of a step of chromatographic separation or of a step of membrane separation.

The step of chromatographic fractionation is carried out in a manner known per se, discontinuously or continuously (simulated moving bed), over adsorbents of the cationic resin type, or over strongly acidic zeolites, preferentially charged by means of alkali metal ions, or more preferentially by means of sodium ions.

Instead of the chromatographic separation step, it is possible to carry out a step of separation by membrane nanofiltration. Membranes with different pore diameters are manufactured from numerous polymers and copolymers of the polysulfone, polyamide, polyacrylonitrate, polycarbonate or polyfuran type.

Examples of the use of such membranes are described especially in documents U.S. Pat. Nos. 4,511,654, 4,429,122 and WO-A-95/10627.

It is also possible to mix the maltose syrup A with an additional starch hydrolyzate syrup, this additional starch hydrolyzate syrup possibly comprising glucose, maltose, and/or other monosaccharides.

According to the process of the invention, it is entirely possible, during step b), to combine at least two steps selected from the steps of concentration, of dilution, of enrichment in maltose and of mixing with an additional starch hydrolyzate syrup; in other words, it is entirely possible, for example, to carry out a step of concentration of the maltose syrup A followed by a step of enrichment in maltose to form a maltose syrup B.

The maltose syrups A and B may, depending on the conditions, have a variable maltose content. The syrup may comprise, relative to the dry weight thereof, at least 30% of maltose, for example from 45 to 99.9%, especially from 50 to 99%.

The process according to the invention also comprises a step c) of hydrogenation of the maltose syrup A or of the maltose syrup B to form an aqueous maltitol composition C.

The maltose syrup may be readily catalytically hydrogenated. The hydrogenation of such a syrup is carried out in accordance with the standard practices in the art, which lead for example to the production of maltitol from maltose and sorbitol from glucose.

For this step, it is equally possible to use ruthenium-based catalysts or Raney nickel catalysts. However, it is preferred to use Raney nickel catalysts, which are less expensive.

In practice, generally 1 to 10% by weight of catalyst is used, relative to the dry matter of the maltose syrup subjected to the hydrogenation. The hydrogenation is preferably carried out on a maltose syrup, the dry matter of which is between 15 and 55%, in practice close to 30 to 50%, under a hydrogen pressure of between 20 and 200 bar. It may be carried out continuously or discontinuously. When it is carried out discontinuously, the hydrogen pressure used may generally be between 30 and 60 bar. The temperature at which the hydrogenation takes place is generally between 100 and 150° C. Care is generally also taken to maintain the pH of the hydrogenation medium by the addition of sodium hydroxide or sodium carbonate for example, but without exceeding a pH of 9.0. This method makes it possible to avoid the appearance of cracking or isomerization products.

The reaction may be stopped when the content of reducing sugars in the reaction medium has become less than 1%, more preferably still less than 0.5% and most particularly less than 0.1%. After cooling the reaction medium, the catalyst is generally removed by filtration, and it is possible to carry out a demineralization over cationic and anionic resins.

At the end of step c), an aqueous maltitol composition C is obtained, this composition generally comprising different polyols, including maltitol. The content in the different polyols mainly depends on the composition in the different monosaccharides of the maltose syrup subjected to hydrogenation.

The process optionally comprises a step d) in which the aqueous maltitol composition C is subjected to a step of concentration, of dilution, of enrichment in maltitol and/or of mixing with an additional polyol syrup.

The methods of concentration, of dilution and of enrichment described for step b) may also be used with a view to carrying out step d). The additional polyol syrup may especially comprise sorbitol, maltitol and/or other polyols.

According to the process of the invention, it is entirely possible, during step d), to combine at least two steps selected from the steps of concentration, of dilution, of enrichment in maltitol and of mixing with an additional polyol syrup; in other words, it is entirely possible, for example, to carry out a step of concentration of the aqueous maltitol composition C followed by a step of enrichment in maltitol.

According to the process of the invention, it is also possible to carry out a step e) of formation of maltitol powder from the maltitol composition C or from the maltitol composition D, via conventionally used methods. This step e) may be carried out by a step of crystallization, optionally combined with a step of texturizing of the powder crystallized in this way.

By way of example of methods for producing maltitol powder, mention may be made of those described in documents EP 2055197 A1, WO 2009112740 A2, EP2093231 A1, EP 905138 A1 and EP 735042 A1.

The process according to the invention comprises a step of recovery f), in which step the maltitol composition C obtained at the end of step c), the maltitol composition D obtained at the end of step d), or the maltitol powder obtained in step e), are recovered.

According to the variant in which the maltitol is in the form of an aqueous composition, the amount by weight of dry maltitol of the aqueous composition, expressed as dry weight, advantageously ranges from 45 to 99.9%, for example from 50 to 99%. Preferably, the dry matter of the aqueous composition ranges from 50 to 95%, especially from 70 to 90%.

The examples which follow make it possible to understand the invention more clearly, without however limiting the scope thereof.

EXAMPLES

Production of Aqueous Solutions of Beta-Amylase

In the production of starch from wheat, a soluble fraction is first collected at the inlet of the solubles evaporator, a step conventionally carried out to produce products intended for feeding livestock, once concentrated. These products are sold by the applicant company under the name Corami®. These soluble fractions have a pH of between 4 and 5 and a beta-amylase activity of about 30° DP/ml.

The microfiltration of soluble fractions of wheat is carried out here on pilot-scale equipment. The microfiltration unit is equipped with ceramic membranes made of titanium oxide, the cut-off threshold of which is equal to 0.2 μm. The permeate flow rate is fixed at 12 l/(h m$^2$). The volume concentration factor is equal to 1.5. The temperature and the pH of the permeate are respectively equal to 45° C. and approximately 4.5.

0.8 l of Neutrase protease (Novozyme) is added to the soluble fraction, at a concentration fixed at 0.1% by volume relative to the total volume of said composition. This protease is left to act beforehand for 1 hour at room temperature.

An ultrafiltration as described above is then carried out.

A microfiltration permeate with a degree DP of 25° DP/ml is obtained after one hour of microfiltration, this degree reflecting the enzymatic activity of the solution containing the δ-amylase. The enzymatic activity measurement is determined through the diastatic activity. The latter is expressed in degrees of diastatic power (° DP), defined as the amount of enzyme contained in 0.1 ml of a 5 wt % solution of a sample of enzyme preparation sufficient to reduce 5 ml of Fehling's solution, when said sample is placed in 100 ml of the substrate for 1 h at 20° C.

The microfiltration step is followed by an ultrafiltration step, carried out on the microfiltration permeate. The main objective thereof is to concentrate said permeate and to remove any contaminating residual salts, sugars and proteins therefrom. The ultrafiltration pilot equipment is equipped with organic membranes made of polysulfone, having a 25 KDa cut-off threshold (Alfa Laval membranes). The filtration temperature is fixed at 25° C. in order to limit bacteriological development as much as possible and to preserve the enzymatic activity. The transmembrane pressure (TMP) is fixed at 4 bar maximum.

An aqueous solution of beta-amylase is then obtained, which consists of the ultrafiltration retentate, having a content by dry weight of beta-amylase which is equal to 15% of the total weight thereof.

Different cocktails, as indicated in tables 1 to 3, were tested. All percentages are expressed as percentage by dry weight of product relative to the total weight of the aqueous solution. Once the preparations are produced, an enzymatic assay of each sample (contained in sterile 100 ml containers) is carried out according to the method described in the patent application FR 2 994 440 (measure of beta-amylase activity). This value serves as reference for the whole study. The different samples are then placed in a temperature-controlled oven: 37° C. for the desired period; a sample is then taken to measure the residual beta-amylase activity at different times (the days on which samples are taken are indicated in tables 1 to 3). The results are given in tables 1 to 3 and are expressed as % of residual beta-amylase activity. The temperature of 37° C. is chosen so as to accelerate the phenomena which bring about the drop in enzymatic activity.

Table 1a demonstrates that the best result is obtained with the mixture of 40% glycerol, 0.2% potassium sorbate and 0.2% Na$_2$CO$_3$. It also demonstrates that compared to other cocktails using other ingredients, it is indeed the solution according to the invention which makes it possible to develop the best degree of stability. This is therefore indeed a non-obvious selection of ingredients to produce a cocktail which leads to surprising and entirely advantageous results in terms of limiting loss of enzymatic activity. Table 1a demonstrates that the cocktails as described in claim 1 of the present application make it possible to develop very high degrees of stability. Regardless of the amounts of constituents of the cocktail, the stability is always at least slightly better, or even much better. The greatest stability is, moreover, obtained with the final cocktail described in this table, produced with the optimal doses of each ingredient, as described in claim 2 of the present application.

Table 2 demonstrates that glycerol, used alone and even at a high dose, does not make it possible to achieve a satisfactory degree of stability. Table 3 demonstrates that the substitution of glycerol with sugars also does not make it possible to achieve a satisfactory degree of stability.

TABLE 1

| Days | 50% glycerol + 0.2% PS | 50% glycerol + 0.2% PS + 1% Na$_2$HPO$_4$ | 40% glycerol + 0.2% PS + 1% Na$_2$CO$_3$ | 40% sorbitol + 0.2% PS + 1% Na$_2$HPO$_4$ | 40% sorbitol + 0.2% PS + 1% CaCO$_3$ | 50% glycerol + 0.2% PS + 1% CaCO$_3$ |
|---|---|---|---|---|---|---|
| 0 | 100 | 100 | 100 | 100 | 100 | 100 |
| 20 | 98 | 98 | | | | |
| 30 | | | 72 | | | |
| 34 | 89 | 89 | | 77 | 85 | 92 |
| 60 | | | 60 | | | |
| 72 | 48 | 70 | 75 | 66 | 69 | 70 |
| 90 | | 45 | 50 | 44 | 45 | 47 |

TABLE 1a

| Days | 60% glycerol + 0.2% PS + 0.4% Na$_2$CO$_3$ | 40% glycerol + 1% PS + 0.4% Na$_2$CO$_3$ | 40% glycerol + 0.2% PS + 0.4% Na$_2$CO$_3$ | 40% glycerol + 0.4% PS + 0.2% Na$_2$CO$_3$ | 40% glycerol + 0.2% PS + 0.2% Na$_2$CO$_3$ |
|---|---|---|---|---|---|
| 0 | 100 | 100 | 100 | 100 | 100 |
| 72 | 74 | 73 | 76 | 76 | 80 |
| 90 | 49 | 48 | 54 | 54 | 60 |

TABLE 2*

| | 0% glycerol | 30% glycerol | 40% glycerol | 50% glycerol |
|---|---|---|---|---|
| 0 | 100 | 100 | 100 | 100 |
| 30 | 0 | 53 | 65 | 69 |
| 60 | 0 | 27 | 44 | 56 |
| 90 | 0 | 7 | 16 | 28 |

TABLE 3

| Days | 50% glucose | 10% glycerol + 30% glucose | 20% glycerol + 20% glucose | 40% glucose + 0.5% Na$_2$HPO$_4$ | 40% glucose + 3% NaCl | 40% maltose | 40% mixture (45% glucose, 10% fructose, 45% maltose) |
|---|---|---|---|---|---|---|---|
| 0 | 100 | 100 | 100 | 100 | 100 | 100 | 100 |
| 30 | 66 | 53 | 61 | 82 | 42 | 46 | 39 |
| 60 | 43 | 35 | 37 | 43 | 15 | 30 | 20 |
| 90 | 28 | 22 | 22 | 22 | 7 | | |

PS: potassium sorbate
*the formation of a large insoluble deposit is also noted in the case of calcium carbonate Production of Maltose Syrups 4 tests are then carried out, relating to the manufacture of maltose syrups from 4 stabilized beta-amylase aqueous solutions. 3 tests according to the invention and 1 reference test are carried out using stabilized solutions having been stored for 90 days at 25° C. before being used.

A starch milk with 31% dry matter is liquefied in the conventional manner by means of 0.2% of an alpha-amylase (TERMAMYL120L sold by Novozymes) at a pH of 5.7 to 6.5 until a DE of approximately equal to 6.

The reaction medium is then heated for a few seconds at 140° C. so as to inhibit the alpha-amylase, then the pH is adjusted to between 5 and 5.5 and the temperature to 55° C.

Saccharification is carried out at 35% dry matter, or slightly below, in the presence of pullulanase (PULLUZYME 750 L sold by ABM) and maltogenic alpha-amylase (MALTOGENASE 4000 L sold by Novozymes) and an aqueous solution of beta-amylase at doses equal to 0.1% of dry matter.

The aqueous solution of beta-amylase consists of the ultrafiltration retentate, having a content by dry weight of beta-amylase which is equal to 15% of the total weight thereof, as described in the preceding example.

In a first test not according to the invention (CP), this solution was stabilized with the cocktail according to the second column of table 1 (50% glycerol+0.2% PS+1% Na$_2$HPO$_4$). The solution remained at a temperature of 25° C. for 90 days before being used as indicated above.

In a second test according to the invention (EX1), this solution was stabilized with the cocktail according to the last column of table 1a (40% glycerol+0.2% PS+0.2% Na$_2$CO$_3$). The solution remained at a temperature of 25° C. for 90 days before being used as indicated above. In a third test according to the invention (EX2), this solution was stabilized with the cocktail according to the fourth column of table 1a (40% glycerol+0.4% PS+0.2% Na$_2$CO$_3$). The solution remained at a temperature of 25° C. for 90 days before being used as indicated above.

In a fourth test according to the invention (EX3), this solution was stabilized with the cocktail according to the third column of table 1 (40% glycerol+0.2% PS+1% Na$_2$CO$_3$). The solution remained at a temperature of 25° C. for 90 days before being used as indicated above.

For these tests, the saccharification, which lasts approximately 72 hours, gives a maltose syrup showing the following compositions for each of the examples:

Maltose Syrup CP:
glucose: 2%, maltose: 77.9%, maltotriose: 5.6%
Maltose Syrup EX1:
glucose: 5%, maltose: 88%, maltotriose: <1.5%
Maltose Syrup EX2:
glucose: 3.2%—maltose: 82.1%—maltotriose: 3.7%
Maltose Syrup EX3:
glucose: 2.8%—maltose: 81%—maltotriose: 4.6%
Production of Maltitol The maltose syrups produced above (CP, EX1, EX2, EX3) are brought to 45% dry matter in an 18 m³ hydrogenator. The temperature is brought to 140° C. and the hydrogen pressure to 60 bar. The pH decreases slowly down to a value of 4.5. At this moment, the pH is raised to 8 by addition of sodium hydroxide. When the content of reducing sugars is less than 0.1% on a dry basis, the reaction is stopped.

The aqueous maltitol composition thus obtained is then purified by demineralization and treatment over activated carbon. This composition is then evaporated to 70% of dry matter. An aqueous maltitol composition is thus obtained having a total reducing sugars content equal to approximately 0.2%.

For each of the compositions, the percentages by weight of sorbitol, maltitol and maltotriitol, expressed as dry matter, are given in the table below.

| Polyol | CP | EX1 | EX2 | EX3 |
| --- | --- | --- | --- | --- |
| % sorbitol | 4 | 7 | 5 | 5 |
| % maltitol | 76 | 86 | 80 | 79 |
| % maltotriitol | 5 | 1.5 | 3.5 | 4 |

It is clearly apparent from the above percentages that it is possible, from the process according to the invention, to improve the richness of the aqueous maltitol compositions. This makes it possible to obtain an excellent maltitol yield from the process, superior to that obtained from a process using, under the same conditions (storage, etc.), a beta-amylase stabilized other than by the combination of stabilizers of use in the invention.

The invention claimed is:

1. A process for producing maltitol, comprising:
   (a) producing a maltose syrup, by hydrolysis of a granular starch, in a first stage of liquefaction of granular starch to form a liquefied starch, followed by a stage of saccharification of the liquefied starch to which an aqueous solution of beta-amylase has been added, to form the maltose syrup A;
   (b) optionally subjecting the maltose syrup A to at least one of concentration, of dilution, of enrichment in maltose, and of mixing with another starch hydrolyzate syrup to form maltose syrup B;
   (c) hydrogenating one of the maltose syrup A and the maltose syrup B to form an aqueous maltitol composition C;
   (d) optionally subjecting the maltitol composition C to at least one of concentration, of dilution, of enrichment in maltitol, of mixing with an additional polyol syrup to form an aqueous maltitol composition D;
   (e) optionally forming maltitol powder from one of the maltitol composition C the maltitol composition D;
   (f) recovering one of the maltitol composition C, the maltitol composition D or the maltitol powder;
   wherein the aqueous solution of beta-amylase has a content by dry weight of beta-amylase of between 5 and 20%, and
   wherein the aqueous solution of beta-amylase also comprises:
      from 0.05 to 0.5% of potassium sorbate;
      from 30 to 50% of glycerol; and
      from 0.05 to 0.5% of sodium carbonate,
      these percentages being expressed as percentage by dry weight of each constituent relative to a total weight of said aqueous solution,
   wherein the saccharification stage is performed in an absence of any active alpha-amylase,
   and wherein the beta-amylase aqueous solution has been stored at room temperature for a time of 60 days up to 300 days before introduction into the liquefied starch.

2. The process according to claim 1, wherein the aqueous solution of beta-amylase comprises:
   (a) from 0.1 to 0.3% potassium sorbate;
   (b) from 35 to 45%, glycerol;
   (c) from 0.1 to 0.3%, sodium carbonate.

3. The process according to claim 1, wherein, the first stage of liquefaction is carried out by enzymatic hydrolysis by means of an alpha-amylase and is followed by an inhibition of the whole active alpha-amylase, by performing a heat shock at a temperature greater than or equal to 130° C., before performing the saccharification stage.

4. The process according to claim 1, wherein the saccharification is carried out in the presence of at least one additional enzyme, selected from the group consisting of maltogenic alpha-amylases, fungal alpha-amylases and debranching enzymes.

5. The process according to claim 1, wherein the maltitol recovered is in the form of an aqueous composition, and the maltitol dry weight of the aqueous composition, expressed as dry weight, ranges from 30 to 99.9%.

6. The process according to claim 1, wherein the beta-amylase aqueous solution is stored for a time of at least one day before introduction into the liquefied starch.

7. The process according to claim 1, wherein the content of reducing sugars in the reaction medium at the end of step c) is less than 1%.

8. The process according to claim 1, wherein each of steps (b), (d), and (e) are conducted.

9. The process according to claim 1, wherein the aqueous solution of beta-amylase consists of:
   0.05 to 0.5 percent by weight potassium sorbate,
   30 to 50 percent by weight glycerol,
   0.05 to 0.5 percent by weight sodium carbonate,
   5 to 20 percent by weight beta-amylase, and
   35 to 50 percent by weight water.

10. The process according to claim 1, wherein the aqueous solution of beta-amylase is prepared by providing a non-stabilized beta-amylase aqueous solution and adding the potassium sorbate, glycerol, and sodium carbonate to the non-stabilized beta-amylase aqueous solution within less than one day after the non-stabilized beta-amylase aqueous solution is formed.

11. The process according to claim 1, wherein the process comprises the step of (b) subjecting the maltose syrup A to at least one of concentration, of dilution, of enrichment in maltose, and of mixing with another starch hydrolyzate syrup to form maltose syrup B.

12. A process for producing maltitol, comprising:
   saccharifying a liquefied starch in the presence of a stored stabilized aqueous solution of beta-amylase, to form maltose syrup A, said stabilized solution comprising potassium sorbate, glycerol, and sodium carbonate, said saccharification being performed in an absence of any active alpha-amylase;

optionally subjecting the maltose syrup A to at least one of concentration, of dilution, of enrichment in maltose, and of mixing with another starch hydrolyzate syrup to form maltose syrup B, hydrogenating one of the maltose syrup A and the maltose syrup B to form an aqueous maltitol composition C;

optionally subjecting the maltitol composition C to at least one of concentration, dilution, enrichment in maltitol, mixing with an additional polyol syrup to form an aqueous maltitol composition D;

optionally forming maltitol powder from one of the maltitol composition C the maltitol composition D;

recovering one of the maltitol composition C, the maltitol composition D and the maltitol powder;

wherein the aqueous solution of beta-amylase has a content by dry weight of beta-amylase of between 5 and 20%, and wherein the aqueous solution of beta-amylase also comprises:

from 0.05 to 0.5% of potassium sorbate;

from 30 to 50% of glycerol; and from 0.05 to 0.5% of sodium carbonate, these percentages being expressed as percentage by dry weight of each constituent relative to a total weight of said aqueous solution, and wherein the beta-amylase aqueous solution has been stored at room temperature for a time of 60 days up to 300 days before introduction into the liquefied starch.

13. The process according to claim 12, wherein the aqueous solution of beta-amylase contains between 10 and 20% beta-amylase by dry weight, from 0.1 to 0.3% potassium sorbate, from 0.1 to 0.3% sodium carbonate and glycerol.

14. The process according to claim 13, wherein the aqueous solution of beta-amylase contains from 35 to 50% by weight water.

15. The process according to claim 12, wherein the process comprises the step of subjecting the maltose syrup A to at least one of concentration, of dilution, of enrichment in maltose, and of mixing with another starch hydrolyzate syrup to form maltose syrup B.

* * * * *